United States Patent [19]

Collins et al.

[11] Patent Number: 4,476,860
[45] Date of Patent: Oct. 16, 1984

[54] SURGICAL DRAPE

[75] Inventors: Robert F. Collins, Barrington, Ill.; Amy S. Paul, Wayland, Mass.

[73] Assignee: The Kendall Company, Boston, Mass.

[21] Appl. No.: 418,328

[22] Filed: Sep. 15, 1982

[51] Int. Cl.³ .............................................. A61B 19/06
[52] U.S. Cl. .................................................. 128/132 D
[58] Field of Search ............... 128/132 D, 132; 2/229, 2/247, DIG. 5, DIG. 7; D2/229

[56] References Cited

U.S. PATENT DOCUMENTS

| D.182,555 | 4/1958 | Vincetz | D2/229 |
| 3,503,391 | 3/1970 | Melges | 128/132 D |
| 3,791,382 | 2/1974 | Collins | 128/132 D |
| 4,105,019 | 8/1978 | Haswell | 128/132 D |

Primary Examiner—Stephen C. Pellegrino
Attorney, Agent, or Firm—Powell L. Sprunger

[57] ABSTRACT

A surgical drape comprising, a main sheet of flexible material having an inner surface for facing toward a patient after placement of the drape, and an outer surface facing away from the patient after placement of the drape. The drape has a pair of pockets of transparent material on the outer surface of the main sheet and having an outer edge defining an opening of the pockets which face toward each other.

13 Claims, 7 Drawing Figures

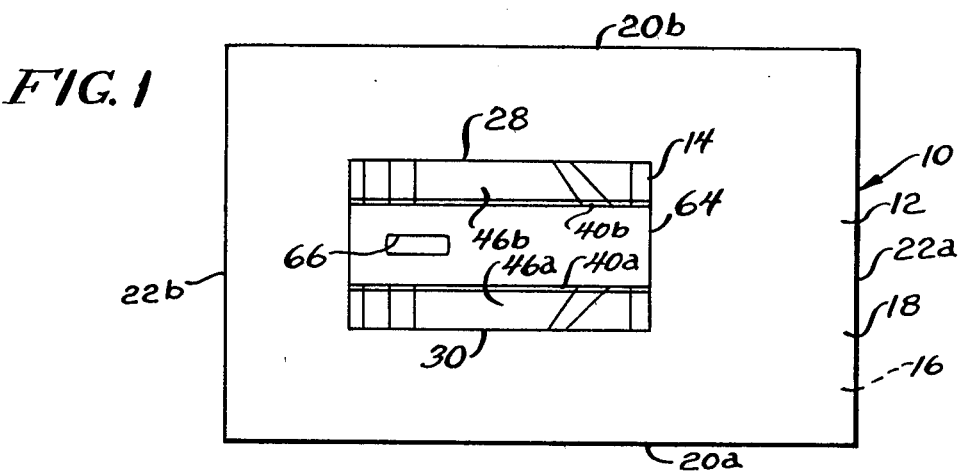
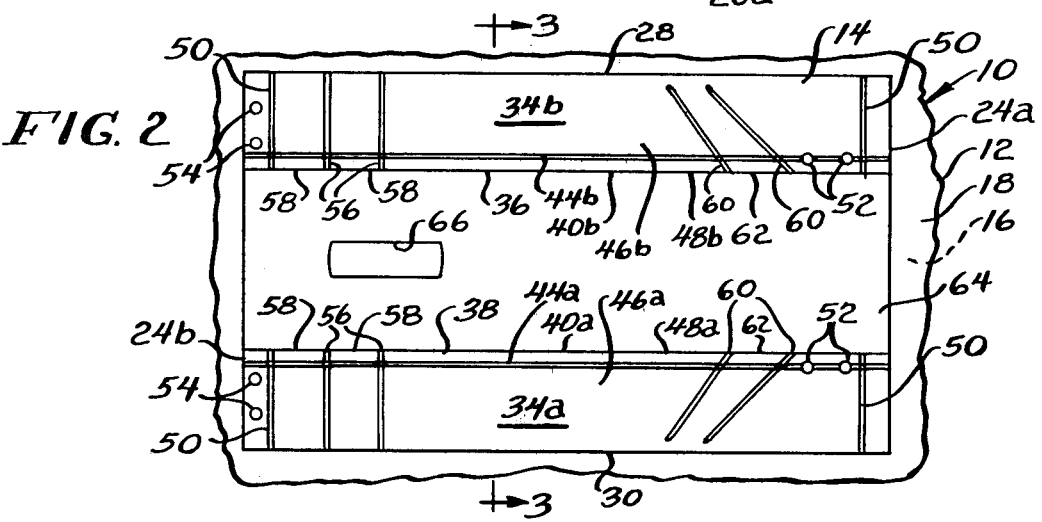
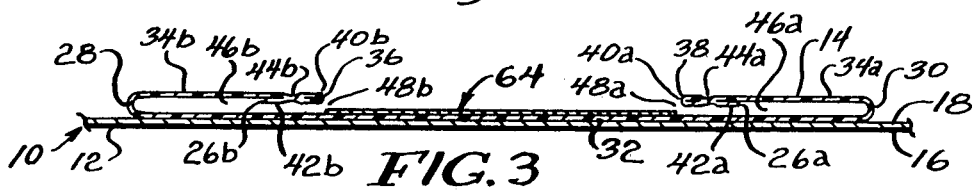
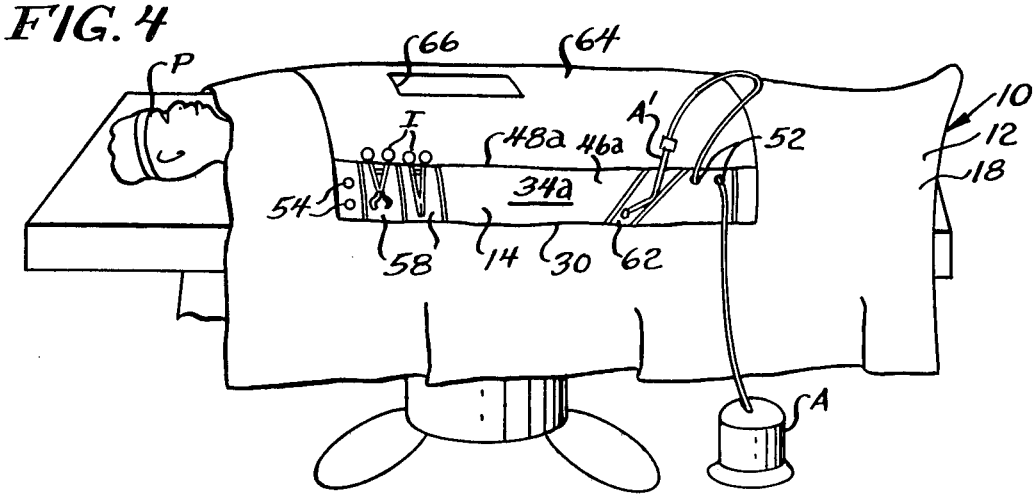

SURGICAL DRAPE

BACKGROUND OF THE INVENTION

The present invention relates to disposable articles, and more particularly to surgical drapes.

Before the present invention, a number of drapes have been known for use during a surgical procedure. For example, in U.S. Pat. No. 3,791,382, incorporated herein by reference, a variety of surgical drapes are disclosed having pockets to catch run-off fluid from a fenestration at the surgical site. However, the pockets of this drape are opaque, and the presence of the pocket contents, such as scalpels, towel clips and sponges, is obscured due to opacity of the pockets. Hence, these articles may be lost or thrown away with the drape. However, the surgeon must find these articles before closing the patient's wound due to a fear of leaving the articles inside the patient, thus causing difficulty to the operating team.

SUMMARY OF THE INVENTION

A principal feature of the present invention is the provision of an improved surgical drape of simplified construction.

The drape of the present invention comprises, a main sheet of flexible material having an inner surface for facing toward a patient after placement of the drape, and an outer surface facing away from the patient after placement of the drape. The drape has a pair of pockets on the outer surface of the main sheet and having an outer edge defining an opening of the pockets which face toward each other.

A feature of the present invention is that the pair of pockets is constructed of a transparent material.

Another feature of the invention is that articles retained in the pockets may be viewed through the transparent material.

Thus, a feature of the present invention is that the presence of articles in the pockets may be detected by the surgical team to prevent their loss.

Another feature of the invention is the provision of lateral seal lines defining compartments in the pockets to retain surgical instruments.

Further features will become more fully apparent in the following description of the embodiments of this invention and from the appended claims.

DESCRIPTION OF THE DRAWINGS

In the drawings:

FIG. 1 is a top plan view of a surgical drape of the present invention;

FIG. 2 is a top plan view taken on an enlarged scale of a transparent sheet of the drape;

FIG. 3 is a fragmentary sectional view taken substantially as indicated along the line 3—3 of FIG. 2; and FIG. 4 is a perspective view illustrating the drape of FIG. 1 in use on a patient.

DESCRIPTION OF THE PREFERRED EMBODIMENTS

Referring now to FIGS. 1-3, there is shown a surgical drape generally designated 10 having a main sheet 12 of flexible material, such as a suitable nonwoven material, and a transparent sheet 14 of flexible material, such as polyethylene. The main sheet 12 has an inner surface 16 for facing toward a patient after placement of the drape 10, and an outer surface 18 for facing away from the patient after placement of the drape 10. The main sheet 12 has a pair of end edges 20a and 20b, and a pair of side edges 22a and 22b connecting the end edges 20a and b.

The transparent sheet 14 has a pair of opposed end edges 24a and 24b, and a pair of opposed side edges 26a and 26b connecting the end edges 24a and b. The transparent sheet 14 has first and second fold lines 28 and 30, respectively, generally aligned with the side edges 26a and b and extending between the end edges 24a and b. The first and second fold lines 28 and 30 define a central panel 32 extending between the first and second fold lines 28 and 30, and define a pair of outer panels 34a and 34b extending from the central panel 32 and being directed toward each other. The central panel 32 is secured to the outer surface 18 of the main sheet 12 by suitable means, such as by adhesive.

The transparent sheet 14 has third and fourth spaced fold lines 36 and 38, respectively, generally aligned and slightly spaced from the side edges 26a and b, with the third and fourth fold lines 36 and 38 extending between the end edges 24a and b. The third and fourth fold lines 36 and 38 define outer edges 40a and 40b of the outer panels 34a and b, respectively, and a pair of edge panels 42a and 42b folded beneath the associated outer panels 34a and b. The edge panels 42a and b are secured to the outer panels 34a and b, respectively, by associated lines 44a and 44b, such as thermal impulse sealing, extending between the end edges 24a and b. As shown, the outer panels 34a and b form a pair of pockets 46a and 46b, respectively, with openings 48a and b facing toward each other and located intermediate the outer edges 40a and b and the central panel 32 communicating with the pockets 46a and b. The transparent sheet 14 has seal lines 50, such as thermal impulse sealing, between the outer panels 34a and b and the central panel 32, with the seal lines 50 extending between the first and second fold lines 28 and 30 and the associated outer edges 40b and 40a adjacent the end edges 24a and b. Thus, the seal lines 50 close the opposed ends of the pockets 46a and b.

The transparent sheet 14 has one or more pairs of spaced openings 52 adjacent the outer edges 40a and b, with the openings 52 extending through the outer panels 34a and b. Also, the transparent sheet 14 may have one or more pairs of spaced openings 54 located intermediate the seal lines 50 and the end edges 24a and b, with the openings 54 extending through the outer panels 34a and b and the central panel 32.

The transparent sheet 14 has one or more lateral seal lines 56, such as thermal impulse sealing, intermediate the outer panels 34a and b and the central panel 32. As shown, the seal lines 56 extend between the first fold line 28 and the outer edge 40b, and between the second fold line 30 and the outer edge 40a. The seal lines 56 and seal line 50 are directed perpendicular to the outer edges 40a and b, and define a plurality of compartments 58 for a purpose which will be described below. The transparent sheet 14 also has a plurality of seal lines 60, such as thermal impulse sealing, between the outer panels 34a and b and the central panel 32. The seal lines 60 extend substantially between the first fold line 28 and the outer edge 40b, and substantially between the second fold line 30 and the outer edge 40a. As shown, the seal lines 60 are disposed at an angle relative to the outer edges 40a and b, and define a pair of compartments 62 for a purpose which will be described below. As shown, ends of the seal lines 60 are spaced slightly from the first and second fold lines 28 and 30 to permit passage of fluid into and out of the pockets. If desired, the seal lines 56 may also be spaced slightly from the first and second fold lines 28 and 30 for a similar purpose.

The drape 10 has a reinforcement sheet 64 secured to an outer surface of the central panel 32, with the reinforcement sheet 64 extending between the outer edges 40a and b, and between the end edges 24a and b of the transparent sheet 14. The reinforcement sheet 64 may be secured to the central panel 32 by suitable means, such as by adhesive, and the reinforcement sheet 64 may comprise an opaque material, such as a sheet of nonwoven material. The drape 10 has a fenestration 66 extending through the main sheet 12, the transparent sheet 14, and the reinforcement sheet 64, with the fenestration 66 being located intermediate the outer edges 40a and b.

With reference to FIGS. 1-4, in use the drape 10 is placed over the patient P with the fenestration 66 located at the site of the surgical procedure. During surgery, the body fluids pass from the surgical site through the fenestration 66 and along the reinforcement sheet 64 through the openings 48a and b into the pockets 46a and b for retention therein. Also, during surgery, the compartments 58 may be utilized to place surgical instruments I therein, such as scalpels, towel clips, and sponges. Hence, the surgical instruments I in the compartments 58 are located for convenient access during the surgical procedure. The openings 52 and 54 may be used to thread a tubing or wire, such as for aspiration equipment A or a cautery device. As shown, the compartments 62 may be also utilized to place surgical instruments therein, such as an aspirator A' from aspiration equipment, in order to place the aspirator A' in a convenient location for use during the surgical procedure. After surgery has been completed, the transparent pockets 46a and b permit vision through the pockets 46a and b in order to detect surgical instruments which might be retained in or have fallen into the pockets 46a and b. Thus, the surgical instruments may be removed from the pockets 46a and b during the tabulation procedure in order to verify that one or more of the surgical instruments have not been left inside the incision of the patient.

The foregoing detailed description is given for clearness of understanding only, and no unnecessary limitations should be understood therefrom, as modifications will be obvious to those skilled in the art.

We claim:
1. A surgical drape, comprising:
a main sheet of flexible material having an inner surface facing toward a patient after placement of the drape, and an outer surface facing away from the patient after placement of the drape; and
a transparent sheet of flexible material having a pair of opposed end edges, a pair of opposed side edges connecting the end edges, first and second spaced fold lines generally aligned with said side edges and extending between said end edges, said first and second fold lines defining a central panel extending between said first and second fold lines and a pair of outer panels extending from said central panel and being directed toward each other, said outer panels having an outer edge defining an opening facing toward each other to form a pair of opposed pockets, said transparent sheet having first seal lines between said outer panels and central panel, with said first seal lines extending between the first and second fold lines and the outer edges at a location adjacent said end edges.

2. The drape of claim 1 wherein said main sheet and transparent sheet have a fenestration intermediate said outer edges.

3. The drape of claim 2 including a reinforcement sheet secured to an outer surface of the transparent sheet intermediate said outer edges.

4. The drape of claim 3 wherein said main sheet, transparent sheet, and reinforcement sheet have a fenestration intermediate said outer edges.

5. The drape of claim 1 including third and fourth spaced fold lines extending between said end edges generally aligned with said side edges, said third and fourth fold lines defining said outer edges and a pair of edge panels folded beneath said outer panels, said third fold line being associated with the first fold line, and the fourth fold line being associated with the second fold line.

6. The drape of claim 5 wherein said edge panels are secured to said outer panels along lines extending between said end edges.

7. The drape of claim 1 including a pair of spaced openings in said transparent sheet to receive tube or wire.

8. The drape of claim 7 wherein said openings are located intermediate said first seal lines and said end edges.

9. The drape of claim 8 wherein said openings are located adjacent said outer edges.

10. The drape of claim 1 including a pair of spaced second seal lines extending substantially between the third fold line and the associated outer edge to define a compartment.

11. The drape of claim 10 wherein the second seal lines are spaced slightly from the third fold line.

12. The drape of claim 10 wherein said second seal lines are approximately perpendicular to said outer edge.

13. The drape of claim 10 wherein said second seal lines are disposed at an angle relative to said outer edge.

* * * * *